(12) United States Patent
Matsuyama et al.

(10) Patent No.: US 6,664,083 B2
(45) Date of Patent: Dec. 16, 2003

(54) METHODS FOR RACEMIZING N-ACYLAMINO ACIDS AND PRODUCING OPTICALLY ACTIVE AMINO ACIDS

(75) Inventors: Akinobu Matsuyama, Ibaraki (JP); Shinji Tokuyama, Shizuoka (JP)

(73) Assignee: Daichel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/794,534

(22) Filed: Feb. 27, 2001

(65) Prior Publication Data

US 2002/0102662 A1 Aug. 1, 2002

(30) Foreign Application Priority Data

Mar. 1, 2000 (JP) ........................................ 2000-060358

(51) Int. Cl.7 ............................ C12P 13/04; C12N 9/90
(52) U.S. Cl. ........................................ 435/106; 435/233
(58) Field of Search ................................... 435/233, 106

(56) References Cited

U.S. PATENT DOCUMENTS

| | | | |
|---|---|---|---|
| 4,525,454 A | 6/1985 | Rozzéll | 435/106 |
| 4,981,799 A | 1/1991 | Takahashi et al. | 435/233 |
| 5,525,501 A | 6/1996 | Tokuyama et al. | 435/233 |
| 6,372,459 B1 * | 4/2002 | Verseck et al. | 435/106 |

OTHER PUBLICATIONS

White, O., et al. (1999) Accession No. F75626.*
Kawarabayasi, Y., et al. (1999) Accession No. H72660.*
Kunst, F., et al. (1999) Accession No. F69991.*
Tokuyama, S., et al. (1995) 42, 884–889.*
Fujita et al., "Cloning of N–acylamino acid recemase gene from *Sebekia benihana* IFO14309", abstracts of the Annual Meeting of the Society for Bioscience and Bioengineering, Japan, p. 166, 1999 (translation attached).

* cited by examiner

Primary Examiner—Charles L. Patterson, Jr.
(74) Attorney, Agent, or Firm—Fish & Richardson P.C.

(57) ABSTRACT

A method for racemizing with N-acylamino acid racemase (NAAR) derived from *Sebekia benihana* and a method for producing optically active amino acids using the racemaization method are provided. The racemase of the present invention can efficiently catalyze the racemization of acylamino acid substrates including N-acylalanine, N-acylaspartic acid, N-acylleucine, and N-acylvaline. Furthermore, this method can be applied to efficient production of optically active amino acids, which are useful, for example, as medicinal raw materials.

25 Claims, 5 Drawing Sheets

SEQUENCE LISTING

```
<160> NUMBER OF SEQ ID NOS: 2

<210> SEQ ID NO 1
<211> LENGTH: 1104
<212> TYPE: DNA
<213> ORGANISM: Sebekia benihana
<220> FEATURE:
<221> NAME/KEY: CDS
<222> LOCATION: (1)..(1101)

<400> SEQUENCE: 1 atg aaa atc acc gga gtg gag ctg cgc cgg atc gcg atg ccg ctg gtc      48
```

```
Met Lys Ile Thr Gly Val Glu Leu Arg Arg Ile Ala Met Pro Leu Val
 1               5                  10                 15 gcg ccg ttc cgc acg tcg ttc ggc acc gag cac gac agg gac gtc ctc    96
Ala Pro Phe Arg Thr Ser Phe Gly Thr Glu His Asp Arg Asp Val Leu
             20                  25                  30 ctg gtc aga gtg gtc acc ccc gat gcc gag ggg tgg ggc gag tgc gtg   144
Leu Val Arg Val Val Thr Pro Asp Ala Glu Gly Trp Gly Glu Cys Val
         35                  40                  45 gcg atg tcg gag ccg ctc tac tcc tcc gag tac gtc gac gga gcc gcc   192
Ala Met Ser Glu Pro Leu Tyr Ser Ser Glu Tyr Val Asp Gly Ala Ala
     50                  55                  60 gcg gtg atc cgc cgc ttc ctg ctg ccc gcg ctg ccc gac aac gtc gac   240
Ala Val Ile Arg Arg Phe Leu Leu Pro Ala Leu Pro Asp Asn Val Asp
 65                  70                  75                  80 gcg tac ggc gtg ggc cac gcc ctc gag ccg atc aag ggc cac cgc atg   288
Ala Tyr Gly Val Gly His Ala Leu Glu Pro Ile Lys Gly His Arg Met
                 85                  90                  95 gcc aag gcg gcg ctg gag acg gcc gtg ctc gac gcc cag ctg agg gcc   336
Ala Lys Ala Ala Leu Glu Thr Ala Val Leu Asp Ala Gln Leu Arg Ala
            100                 105                 110 tcg ggc gag tcg ttc ggc cag ttc ctc ggc gcc acg agg gac agg gtg   384
Ser Gly Glu Ser Phe Gly Gln Phe Leu Gly Ala Thr Arg Asp Arg Val
        115                 120                 125 ccg tgc ggg gtg tcg gtc ggc atc atg gac tcc atc ccg cag ctg ctc   432
Pro Cys Gly Val Ser Val Gly Ile Met Asp Ser Ile Pro Gln Leu Leu
    130                 135                 140 gag gcg gtg gag ggc tat ctg gac gag ggc tac gtc agg atc aag ctg   480
Glu Ala Val Glu Gly Tyr Leu Asp Glu Gly Tyr Val Arg Ile Lys Leu
145                 150                 155                 160 aag atc gag ccc ggc tgg gac gtc gag ccg gtg cgc gcg gtc agg gag   528
Lys Ile Glu Pro Gly Trp Asp Val Glu Pro Val Arg Ala Val Arg Glu
                165                 170                 175 cgg ttc ggc gac gag gtg ttg ctg cag gtc gac gcg aac gcc gcc tac   576
Arg Phe Gly Asp Glu Val Leu Leu Gln Val Asp Ala Asn Ala Ala Tyr
            180                 185                 190 acc ctg gtc gac gcc cag cag ctg gcc agg ctc gac gac ttc ggc ctg   624
Thr Leu Val Asp Ala Gln Gln Leu Ala Arg Leu Asp Asp Phe Gly Leu
        195                 200                 205 ctg ctg atc gag cag ccg ctg gcg aac gac gac ctg gtg cag cac gcc   672
Leu Leu Ile Glu Gln Pro Leu Ala Asn Asp Asp Leu Val Gln His Ala
    210                 215                 220 gag ctg gcc aag cgc ctg cgc acc ccg atc tgc ctg gat gag tcg atc   720
Glu Leu Ala Lys Arg Leu Arg Thr Pro Ile Cys Leu Asp Glu Ser Ile
225                 230                 235                 240 gag tcg gcc gag cac gcg gcg gcc gcc atc tcg ctc aag gcc tgc tcg   768
Glu Ser Ala Glu His Ala Ala Ala Ala Ile Ser Leu Lys Ala Cys Ser
                245                 250                 255 atc gtc aac atc aag ccg ggc agg atc ggc gga tac ctg gag gcg cgg   816
Ile Val Asn Ile Lys Pro Gly Arg Ile Gly Gly Tyr Leu Glu Ala Arg
            260                 265                 270 cgc atc cac gac ctg tgc agg gcg cac ggc atc gcg gtg tgg tgc ggg   864
Arg Ile His Asp Leu Cys Arg Ala His Gly Ile Ala Val Trp Cys Gly
        275                 280                 285 ggc atg ctg gag acg ggc ctc ggc agg gcc gcc aac gtg gcg ctg gcc   912
Gly Met Leu Glu Thr Gly Leu Gly Arg Ala Ala Asn Val Ala Leu Ala
    290                 295                 300 gcg ctg ccc ggc ttc acc ctg ccg ggc gac acc tca ggc tcg cgc cgt   960
Ala Leu Pro Gly Phe Thr Leu Pro Gly Asp Thr Ser Gly Ser Arg Arg
305                 310                 315                 320
```

```
tac tac gcc acc gac atc acc gag ccc ttc gag ctc gac ggc ggc cac    1008
Tyr Tyr Ala Thr Asp Ile Thr Glu Pro Phe Glu Leu Asp Gly Gly His
            325                 330                 335 ctc acc gtg ccg tcg ggc ccc ggc ctg ggc gtc gat ccc gtc aag gag    1056
Leu Thr Val Pro Ser Gly Pro Gly Leu Gly Val Asp Pro Val Lys Glu
        340                 345                 350 atc ctc gag gag gtc acc acc tcg acg gag tgg atc ccg ctc ggc tga    1104
Ile Leu Glu Glu Val Thr Thr Ser Thr Glu Trp Ile Pro Leu Gly
    355                 360                 365
```

<210> SEQ ID NO 2
<211> LENGTH: 367
<212> TYPE: PRT
<213> ORGANISM: Sebekia benihana

<400> SEQUENCE: 2

```
Met Lys Ile Thr Gly Val Glu Leu Arg Ile Ala Met Pro Leu Val
 1               5                  10                  15

Ala Pro Phe Arg Thr Ser Phe Gly Thr Glu His Asp Arg Asp Val Leu
                20                  25                  30

Leu Val Arg Val Val Thr Pro Asp Ala Glu Gly Trp Gly Glu Cys Val
            35                  40                  45

Ala Met Ser Glu Pro Leu Tyr Ser Ser Glu Tyr Val Asp Gly Ala Ala
        50                  55                  60

Ala Val Ile Arg Arg Phe Leu Pro Ala Leu Pro Asp Asn Val Asp
65                  70                  75                  80

Ala Tyr Gly Val Gly His Ala Leu Glu Pro Ile Lys Gly His Arg Met
                85                  90                  95

Ala Lys Ala Ala Leu Glu Thr Ala Val Leu Asp Ala Gln Leu Arg Ala
            100                 105                 110

Ser Gly Glu Ser Phe Gly Gln Phe Leu Gly Ala Thr Arg Asp Arg Val
        115                 120                 125

Pro Cys Gly Val Ser Val Gly Ile Met Asp Ser Ile Pro Gln Leu Leu
    130                 135                 140

Glu Ala Val Glu Gly Tyr Leu Asp Glu Gly Tyr Val Arg Ile Lys Leu
145                 150                 155                 160

Lys Ile Glu Pro Gly Trp Asp Val Glu Pro Val Arg Ala Val Arg Glu
                165                 170                 175

Arg Phe Gly Asp Glu Val Leu Leu Gln Val Asp Ala Asn Ala Ala Tyr
            180                 185                 190

Thr Leu Val Asp Ala Gln Gln Leu Ala Arg Leu Asp Asp Phe Gly Leu
        195                 200                 205

Leu Leu Ile Glu Gln Pro Leu Ala Asn Asp Asp Leu Val Gln His Ala
    210                 215                 220

Glu Leu Ala Lys Arg Leu Arg Thr Pro Ile Cys Leu Asp Glu Ser Ile
225                 230                 235                 240

Glu Ser Ala Glu His Ala Ala Ala Ile Ser Leu Lys Ala Cys Ser
                245                 250                 255

Ile Val Asn Ile Lys Pro Gly Arg Ile Gly Gly Tyr Leu Glu Ala Arg
            260                 265                 270

Arg Ile His Asp Leu Cys Arg Ala His Gly Ile Ala Val Trp Cys Gly
        275                 280                 285

Gly Met Leu Glu Thr Gly Leu Gly Arg Ala Ala Asn Val Ala Leu Ala
    290                 295                 300

Ala Leu Pro Gly Phe Thr Leu Pro Gly Asp Thr Ser Gly Ser Arg Arg
305                 310                 315                 320
```

-continued

```
Tyr Tyr Ala Thr Asp Ile Thr Glu Pro Phe Glu Leu Asp Gly Gly His
            325                 330                 335

Leu Thr Val Pro Ser Gly Pro Gly Leu Gly Val Asp Pro Val Lys Glu
            340                 345                 350

Ile Leu Glu Glu Val Thr Thr Ser Thr Glu Trp Ile Pro Leu Gly
        355                 360                 365
```

US 6,664,083 B2

METHODS FOR RACEMIZING N-ACYLAMINO ACIDS AND PRODUCING OPTICALLY ACTIVE AMINO ACIDS

FIELD OF THE INVENTION

The present invention relates to a method for racemizing N-acylamino acids using racemase, and further, a method for reacting the racemized N-acylamino acids with L-aminoacylase or D-aminoacylase to produce optically active amino acids corresponding to the respective amino acid species.

BACKGROUND OF THE INVENTION

N-acylamino acid racemase (hereinafter, abbreviated to "NAAR") does not react with amino acids but specifically racemizes N-acylamino acids. Enzymes with NAAR activity have been found in Actinomycetes including the genera Streptomyces, Amycolatopsis, and Sebekia (Japanese Patent No. 2712331). A strain, Amycolatopsis sp. TS-1-60, which produces an acylamino acid racemase, a method for producing this enzyme (Unexamined Published Japanese Patent Application (JP-A) No. Hei 6-205668), and a DNA fragment encoding the acylamino acid racemase derived from this strain (JP-A Hei 4-365482) have been disclosed. However, only two NAARs, one of which is derived from Streptomyces sp. Y-53 and the other from Amycolatopsis sp. TS-1-60, have been isolated and purified, and their substrate specificity have been clarified.

Both of these NAARs catalyze only limited types of acylamino acids depending on their substrate specificity. The activity of NAAR derived from Streptomyces sp. Y-53, when the activity on N-acylmethionine is taken as 100, is 50 or higher on N-acylleucine, N-acylphenylalanine, and N-acylvaline, but less than 50 on N-acyltryptophan, N-acylalanine, and N-acylaspartic acid. In addition, the activity of NAAR derived from Amycolatopsis sp. TS-1-60, when the activity on N-acylmethionine is taken as 100, is 50 or higher on N-acylphenylalanine and N-acylvaline but less than 50 on N-acyltryptophan, N-acylalanine, N-acylaspartic acid, and N-acylleucine.

The present inventors previously succeeded in isolating the NAAR gene from *Sebekia benihana* and in expressing the recombinants thereof (Abstracts of the annual meeting of the Society for Bioscience and Bioengineering, Japan, 1999, p. 166). Although *S. benihana* is known to have N-acylamino acid racemase activity on N-acyl-L-methionine, the substrate specificity of the enzyme has not specifically demonstrated.

Racemization of acylamino acids is an important step for producing optically active amino acids. Enzymes have excellent catalytic functions with substrate specificity, reaction specificity, and stereospecificity. Stereospecificity of enzymes, with some exceptions, are nearly absolute.

Recent precise research has increased the importance of optically active substances for use in drugs, pesticides, feeds, and perfumes. Since optical isomers sometimes have quite different biological activities, techniques for specifically obtaining one particular isomer are important. For example, D(R)-form thalidomide has no teratogenic activity, but its L(S)-form shows strong teratogenicity. In fact, the use of thalidomide racemate caused the drug injury incidents by thalidomide. In case where one enantiomer shows an effective biological activity and the other enantiomers have no such activity, coexistence of these enantiomers may not only reduce the total activity but also inhibit the activity of the effective enantiomer competitively. As a result, the biological activity of the racemate is reduced to half or less of the activity of the effective enantiomer. Accordingly, it is industrially important to obtain (synthesize or optically resolve) optically pure enantiomers.

For this objective, a method in which racemates are synthesized and then optically resolved has been widely used. However, an unnecessary enantiomer is always produced as a by-product with the procedure of resolution after synthesis; a problem of efficiently utilizing the raw material remains unsolved. Even if the recovered by-product is reused as the raw material, a definite amount of the by-product is always produced. Therefore, enzymatic optical resolution has drawn attention because it does not produce by-products and a bulk of liquid waste. Enzymatic optical resolution is a method of specifically producing a desired enantiomer by utilizing enzyme specificity. Since unnecessary enantiomers are barely synthesized by this method, it is easy to obtain products of high optical purity. In addition, this method is also advantageous in efficiently utilizing the raw material. The racemase activity is useful for synthesizing racemates as substrates to be used either in optical resolution or in enzymatic synthesis of specific enantiomers. Thus, NAAR is required for catalyzing racemization of acylamino acids.

For example, D-tryptophan is one of important D-amino acids used as medicinal raw materials, etc. D-tryptophan can be obtained by deacylating N-acyl-DL-tryptophan. However, racemase capable of efficiently catalyzing racemization of N-acyltryptophan to N-acyl-DL-tryptophan is not yet known. Similarly, racemase efficiently catalyzing racemization using, as a substrate, an acylamino acid, such as N-acylalanine, N-acylaspartic acid, N-acylleucine or N-acylvaline is not yet known.

SUMMARY OF THE INVENTION

An objective of the present invention is to provide a method for racemizing N-acylamino acids using a racemase exhibiting racemization activity on a wide variety of substrates and a method for producing optically active amino acids using the racemization method.

In order to achieve these objectives, the present inventors searched for racemases effectively catalyzing a wide variety of substrates. Then, the present inventors have found that the NAAR derived from *Sebekia benihana*, which was previously reported by the inventors, has the substrate specificity that is industrially available for racemization of N-acylamino acids, thereby completing the present invention. Specifically, the present invention relates to a method for racemizing N-acylamino acid using NAAR having particular substrate specificity and a method for producing optically active amino acids using the racemization method. More specifically, it relates to:

[1] A method for racemizing an N-acylamino acid, the method comprising contacting an N-acylamino acid racemase or a processed product thereof with an optically active N-acylamino acid to racemize the N-acylamino acid, wherein the racemase comprises a polypeptide selected from the group consisting of:
  (a) a polypeptide comprising the amino acid sequence of SEQ ID NO: 2;
  (b) a polypeptide comprising the amino acid sequence of SEQ ID NO: 2 in which one or more amino acids are substituted, deleted, inserted, and/or added, and having activity of an N-acylamino acid racemase having activity of an N-acylamino acid racemase having enzymatic properties of (1) and (2) below; and (c) a polypeptide encoded by a polynucleotide hybridizing to a DNA comprising the nucleotide sequence of SEQ ID NO: 1 under stringent conditions, and having activity of an N-acylamino acid racemase having enzymatic properties of (1) and (2) below;

(1) action: the racemase racemizes N-acylamino acids and (2) substrate specificity: the racemase has relative activity of at least 50 or higher for each of N-acylalanine, N-acylaspartic acid, N-acylleucine, N-acylvaline, and N-acyltryptophan among N-acylamino acids when the activity for N-acylmethionine is taken as 100.

[2] A method for racemizing an N-acylamino acid, the method comprising contacting a microorganism producing a racemase or a processed product of the microorganism with an optically active N-acylamino acid to racemize the N-acylamino acid, wherein the microorganism is a transformant expressing a polypeptide encoded by a polynucleotide selected from the group consisting of:

(a) a polynucleotide comprising the coding region of the nucleotide sequence of SEQ ID NO:1;

(b) a polynucleotide encoding a polypeptide comprising the amino acid sequence of SEQ ID NO:2;

(c) a polynucleotide hybridizing to a DNA comprising the nucleotide sequence of SEQ ID NO:1 under stringent conditions, wherein the polynucleotide encodes a polypeptide having activity of an N-acylamino acid racemase having enzymatic properties of (1) and (2) below; and (d) a polynucleotide encoding a polypeptide comprising the amino acid sequence of SEQ ID NO:2 in which one or more amino acids are substituted, deleted, inserted, and/or added, and having activity of an N-acylamino acid racemase having enzymatic properties of (1) and (2) below;

(1) action: the racemase racemizes N-acylamino acids and (2) substrate specificity: the racemase has relative activity of at least 50 or higher for each of N-acylalanine, N-acylaspartic acid, N-acylleucine, N-acylvaline, and N-acyltryptophan among N-acylamino acids when the activity for N-acylmethionine is taken as 100.

[3] The method according to [1] or [2], wherein the N-acylamino acid is at least one N-acylamino acid selected from the group consisting of N-acylalanine, N-acylaspartic acid, N-acylleucine, N-acylvaline, and N-acyltryptophan.

[4] A method for producing a D- or L-amino acid, the method comprising racemizing an N-acyl-DL-amino acid by the method according to [1] or [2] in the presence of a D- or L-aminoacylase.

DETAILED DESCRIPTION OF THE INVENTION

Figure 1:
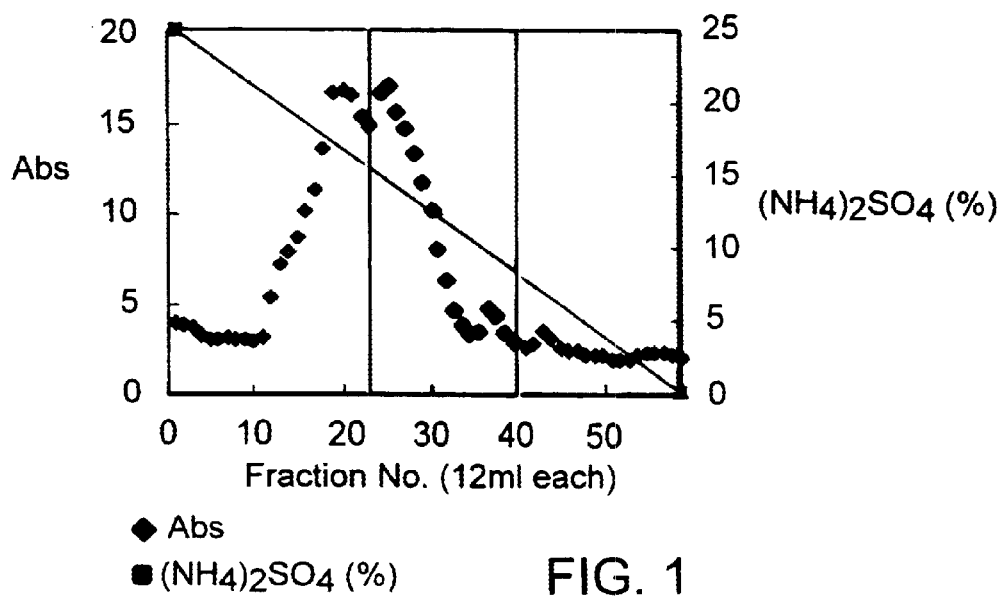
FIG. 1 shows a chromatogram of a first round Butyl-Toyopearl 650M chromatography of a crude enzyme obtained from *Escherichia coli* transformed with an NAAR-expression vector. The left and right handed vertical axes indicate the absorbance at 280 nm and $(NH_4)_2SO_4$ concentration (%), respectively, and the horizontal axis indicates the fraction numbers.

The present invention provides a method for racemizing an N-acylamino acid using an NAAR comprising a polypeptide selected from the group consisting of:

(a) a polypeptide comprising the amino acid sequence of SEQ ID NO:2;

(b) a polypeptide comprising the amino acid sequence of SEQ ID NO:2 in which one or more amino acids are substituted, deleted, inserted, and/or added, and having activity of an N-acylamino acid racemase having enzymatic properties of (1) and (2) below; and (c) a polypeptide encoded by a polynucleotide hybridizing to a DNA comprising the nucleotide sequence of SEQ ID NO:1 under stringent conditions, and having activity of an N-acylamino acid racemase having enzymatic properties of (1) and (2) below;

(1) action: the racemase racemizes N-acylamino acids and (2) substrate specificity: the racemase has relative activity of at least 50 or higher for each of N-acylalanine, N-acylaspartic acid, N-acylleucine, N-acylvaline, and N-acyltryptophan among N-acylamino acids when the activity for N-acylmethionine is taken as 100.

The NAAR comprising the amino acid sequence of SEQ ID NO:2 can be isolated from *Sebekia benihana*. *S. benihana* is available, for example, as a strain of IFO 14309. This strain is recited in the List of Cultures 10th edition (1996) published by Institute of Fermentation Research, Osaka (IFO) and is available from IFO. More specifically, NAAR can be purified from *S. benihana* cultured by a known method. For example, the bacterial cells are disrupted, and then precipitated with protamine sulfate, followed by centrifugation. The supernatant is subjected to salting-out with ammonium sulfate and further purified by any combination of anion-exchange chromatography, hydrophobic chromatography, affinity chromatography, and gel filtration.

The NAAR purified from *S. benihana* IFO 14309 has the enzymatic properties of (1) to (6) below:

(1) action: the racemase racemizes N-acylamino acids and (2) substrate specificity: the racemase has relative activity of at least 50 or higher for each of N-acylalanine, N-acylaspartic acid, N-acylleucine, N-acylvaline, and N-acyltryptophan among N-acylamino acids when the activity for N-acylmethionine is taken as 100.

(3) molecular weight: the molecular weight of the enzyme is about 44,000 daltons estimated by SDS-PAGE, and about 340,000 daltons estimated by gel filtration;

(4) inhibitor: the enzyme is inhibited by PCMB;

(5) optimal temperature range for the reaction: the optimal temperature is 40 to 60° C; and (6) stable pH range: the enzyme is stable between pH 7.5 and 10.

The NAAR of the present invention can be a recombinant polypeptide obtained by expressing a polynucleotide encoding the NAAR. The NAAR of the present invention may be the polypeptide of (b) or (c) as well as (a) above. Whether a polypeptide comprising the amino acid sequence of the NAAR purified from *S. benihana* IFO 14309 (SEQ ID NO:2) in which one or more amino acids are substituted, deleted, inserted, and/or added has the enzyme activity similar to that of the NAAR comprising the amino acid sequence of SEQ ID NO:2 can be determined by comparing the racemase activity of such a polypeptide with that of the above NAAR using the method described later. Those skilled in the art can thus readily select NAAR homologues usable in the present invention.

The number of amino acids that are mutated is not particularly restricted, as long as the NAAR activity is maintained. Normally, it is within 50 amino acids, preferably within 30 amino acids, more preferably within 10 amino acids, and even more preferably within 3 amino acids. The site of mutation may be any site, as long as the NAAR activity is maintained.

An amino acid substitution is preferably mutated into different amino acid(s) in which the properties of the amino acid side-chain are conserved. A "conservative amino acid substitution" is a replacement of one amino acid residue belonging to one of the following groups having a chemically similar side chain with another amino acid in the same group. Groups of amino acid residues having similar side chains have been defined in the art. These groups include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

The homologue of the polypeptide comprising the amino acid sequence of SEQ ID NO:2 includes a polypeptide exhibiting percent identity of at least 70%, preferably at least 80% or 90%, more preferably 95% or more to the amino acid sequence of SEQ ID NO:2. As used herein, "percent identity" of two amino acid sequences or of two nucleic acids is determined using the algorithm of Karlin and Altschul (Proc. Natl. Acad. Sci. USA 87:2264–2268, 1990) modified as in Karlin and Altschul (Proc. Natl. Acad. Sci. USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score= 100, wordlength=12. Homology search of protein can readily be performed, for example, in DNA Databank of JAPAN (DDBJ), by using the FASTA program, BLAST program, etc. BLAST protein searches are performed with the XBLAST program, score=50, wordlength=3. Where gaps exist between two sequences, Gapped BLAST is utilized as described in Altsuchl et al. (Nucleic Acids Res. 25:3389–3402, 1997). When utilizing BLAST and Gapped BLAST programs, the default parameters of the respective programs (e.g, XBLAST and NBLAST) are used. See http://www.ncbi.nlm.nih.gov.

Further, a polypeptide encoded by a polynucleotide hybridizing to a DNA comprising the nucleotide sequence of SEQ ID NO:1 under stringent conditions and having the enzymatic properties of (1) and (2) above can be used as an NAAR of the present invention. Polypeptides encoded by polynucleotides hybridizing to the DNA encoding the NAAR isolated from *S. benihana* IFO 14309 under stringent conditions include polypeptides with enzymatic activity similar to that of the above-mentioned NAAR. Those skilled in the art can readily select NAAR homologues usable in the present invention from such enzymes by the method described below.

The homologue of the polynucleotide comprising the nucleotide sequence of SEQ ID NO:1 includes a DNA encoding a polypeptide exhibiting percent identity of at least 70%, preferably at least 80% or 90%, more preferably 95% or more to the amino acid sequence of SEQ ID NO:2. Determination of percent identity of two amino acid sequences or of two nucleic acids and homology search can be performed as described above.

In the selection of the NAAR homologues of the present invention, the racemase activity on N-acylamino acids can be measured as follows. The reaction solution containing Tris-HCl buffer (pH 7.5, 50 mM), cobalt chloride (1.0 mM), an N-acylamino acid (20 mM), and the enzyme is incubated for 5 minutes at 30° C., and the solution is then heated for 5 minutes at 100° C. to stop the reaction. After that, 3 U of L-aminoacylase is added and allowed to react for 1 hour at 30° C., and the solution is then heated for 3 minutes at 100° C. to stop the reaction. Subsequently, the solution is centrifuged at 15,000 rpm for 10 minutes at 4° C., and the amino acid produced is assayed by TNBS method. In this assay, 1 U is defined as the amount of enzyme required for racemization of 1 $\mu$mol of an N-acylamino acid in a minute. Quantification of polypeptide is carried out by a dye-binding method using the Bio-Rad protein assay kit (Bio-Rad Co.). Procedures of TNBS method are as follows: 0.5 ml of 100 mM $Na_2B_4O_7$ is mixed with 0.5 ml of a sample containing the amino acid; then 20 $\mu$l of 110 mM TNBS (trinitrobenzenesulfonic acid) solution is added and stirred immediately; after 5 minutes, 2 ml of 100 mM $NaHPO_4$ containing 1.5 mM $Na_2SO_3$ is added to the mixture to stop the coloring reaction; and then absorbance is measured at a wavelength of 420 nm.

The term "polynucleotide hybridizing under stringent conditions" means a DNA to which a probe DNA hybridizes under the conditions indicated in the protocol provided by the supplier (washing with the primary wash buffer containing 0.5× SSC at 42° C.) using, for example, the ECL direct nucleic acid labeling and detection system (Amersham Pharmacia Biotech Co.). DNA to be used as probe DNA can be one or more consecutive sequences consisting of at least 20 residues, preferably at least 30, for example, 40, 60, or 100 nucleotides arbitrarily selected from the nucleotide sequence of SEQ ID NO:1.

The nucleotide sequence of SEQ ID NO:1 is that of the DNA encoding NAAR isolated from *S. benihana* IFO 14309. This DNA can be obtained by PCR using a genomic library or cDNA library of *S. benihana* as a template. The primers required for the PCR can be readily designed by one skilled in the art on the basis of the nucleotide sequence of SEQ ID NO:1. Alternatively, the DNA can be obtained by screening the genomic library or cDNA library using a DNA probe comprising a nucleotide sequence selected from the nucleotide sequence of SEQ ID NO:1. The methods for cloning genes based on PCR and probe hybridization are well known.

Specifically, genomic DNA is prepared by culturing a microorganism of the genus Sebekia that is capable of producing N-acylamino-acid racemase, and then by converting its cells into spheroplasts with a cell wall-digesting enzyme, followed by a standard method (for example, J. Biol. Chem. 268:26212–26219 (1993); Meth. Cell. Biol. 29:39–44 (1975)). *S. benihana* IFO 14309 can be used as the microorganism. The chromosomal DNA thus prepared is completely or partially digested into about 2- to 8-kb DNA fragments with appropriate restriction enzymes (e.g., HindIII, EcoRI, BamHI, Sau3AI, etc.). The digested genomic DNA is subjected to Southern hybridization using a probe designed on the basis of the sequence of SEQ ID NO:1, to form a hybrid between the DNA fragment of interest and the probe. Multiple DNA fragments that hybridized to the probe are recovered and then inserted into an *E. coli* expression vector.

*E. coli* (e.g. *E. coli* strain JM109, etc) is transformed with the resulting recombinant plasmid to prepare a genomic library. Plasmids including pUC18 (Takara Shuzo), pKK223-3 (Pharmacia), pET derivatives (Takara Shuzo or others), or pMAL-p2 (NEB) can be used as expression vectors. The genomic library is screened for positive colonies by colony hybridization using the same probe as used above. Plasmids are extracted from the positive colonies and then digested with restriction enzymes to recover the insert DNA of interest. With the same probe, Southern hybridization is performed to confirm the gene of interest by forming hybrid between the insert DNA and the probe. The nucleotide sequence of the insert is further determined by sequencing and compared with the nucleotide sequence of SEQ ID NO:1 to confirm whether the gene of interest has been successfully isolated. The DNA thus obtained is used to transform a host cell after inserted into an appropriate expression vector to give a strain overexpressing the NAAR encoded by the DNA. Such an overexpression strain can be used for manufacturing optically active amino acids in the method of the present invention.

The NAAR can be purified from the NAAR-overexpressing strain. Specifically, the gene for the enzyme is expressed in the above-mentioned overexpression strain cultured under the conditions that can induce the NAAR expression. The cultured cells are collected and lysed, and the supernatant obtained can be used as a crude enzyme solution for the enzymatic reaction. Alternatively, the NAAR can be purified according to the method as described above.

The NAAR activity in the crude enzyme solution can be determined as follows. Specifically, the crude enzyme is reacted with N-acetyl-D-methionine as a substrate in the presence of L-amino acylase for 5 to 60 hours at 30° C., and the N-acylamino acid racemase activity is determined by measuring the production of L-methionine. The amount of enzyme required for the production of 1 µmol of L-methionine in a minute is defined as 1 U. The production of methionine can be verified qualitatively by thin layer chromatography (TLC).

Microorganisms having the ability to produce N-acylamino acid racemase and being used as a genetic source in the above-described cloning include any strains belonging to the genus Sebekia and having the ability to produce N-acylamino acid racemase as well as mutants and variants thereof. Among them, *Sebekia benihana* is one of the particularly preferable species.

When the open reading frame is ligated into an *E. coli* expression vector, for example, pUC18, pKK223-3, pET, pMAL-p2, or the like, at a downstream site of the promoter in forward orientation, N-acylamino acid racemase derived from Sebekia can be expressed as a native protein or a fusion protein.

The present invention provides a method for racemizing N-acylamino acid using the above-mentioned NAAR. The desired enzyme reaction can be conducted by contacting the above-mentioned NAAR, a microorganism overexpressing the enzyme, or a processed product of these, with a reaction solution containing N-acylamino acid. Specifically, the reaction can be carried out in water or in a water-insoluble organic solvent, for example, ethyl acetate, butyl acetate, toluene, chloroform, n-hexane, and the like, or in a mixture of an aqueous medium and the organic solvent. The racemization method according to the present invention can be carried out using an immobilized enzyme or a membrane reactor. The mode of contacting the enzyme with the reaction solution is not limited to these specific examples. The term "reaction solution" means a solution in which a substrate is dissolved in a solvent that gives a desirable environment for the enzyme to exert its activity.

In the present invention, a processed product of a microorganism containing NAAR specifically includes microorganisms that are treated by detergent or organic solvent such as toluene to alter the permeability of the cell membrane, as well as a cell-free extract prepared by disrupting the cells with glass beads or by enzyme treatment and partially purified product of the cell-free extract. A processed product of NAAR includes NAAR immobilized on an insoluble carrier by a known method. The NAAR of the present invention is not limited to purified NAAR, but other forms such as a crude enzyme can also be used.

An N-acylamino acid used for the racemization method of the present invention may be represented by the following formula (1):

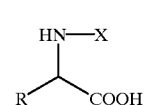

(1)

where X represents a substituted or unsubstituted acyl group derived from a carboxylic acid and R represents a substituted or unsubstituted alkyl group having 1 to 20 carbon atoms.

The acyl group (X) of the N-acylamino acid may have a substituent (i.e., halogen, alkyl, alkoxy, etc.), including carboxylic acyl groups such as alkanoyl (i.e., formyl, acetyl, chloroacetyl, etc.); benzoyl (i.e., benzoyl, p-chlorobenzoyl, etc.); arylalkanoyl (i.e., phenylacetyl, phenylpropionyl, etc.).

The alkyl group represented by R includes a $C_{1-4}$ alkyl group that is substituted with linear or branched alkyl, hydroxylalkyl, $C_{1-3}$ alkylthio, thiol, phenyl, hydroxyphenyl, or indolyl; and $C_{1-4}$ alkyl group that is substituted with amino, carboxyl, guanidyl, or imidazolyl; etc.

More specifically, N-acylalanine, N-acylaspartic acid, N-acylleucine, N-acylvaline, and N-acyltryptophan, which have particularly high reactivity, are used preferably.

Racemization reaction of the present invention can be carried out at a reaction temperature of 4 to 60° C., preferably 10 to 40° C.; at pH 3 to 11, preferably pH 6 to 9; at a substrate concentration of 0.01 to 90%, preferably 0.1 to 30%. The reaction often proceeds in a yield of 50 to 100%. The substrate can be added at once at the start of the reaction, but it is preferable to add the substrate successively or discretely to prevent the substrate concentration in the reaction solution from getting too high.

In addition, the present invention relates to a method for producing optically active amino acids by the combined use of the above-mentioned NAAR and L- or D-aminoacylase. Specifically, the above-mentioned NAAR, a microorganism producing this enzyme, or a processed product of these is reacted with N-acylamino acids, with which L- or D-aminoacylase is further reacted, to produce optically active amino acids as the reaction products. The reaction can be performed in the presence of both of the NAAR and L- or D-aminoacylase. The method for producing optically active amino acids of the present invention can be conducted in water or in a water-insoluble organic solvent, such as ethyl acetate, butyl acetate, toluene, chloroform, n-hexane, etc, or in a mixture of an aqueous medium and the organic solvent. A racemization method of the present invention can be carried out using an immobilized enzyme or a membrane reactor.

The method of the present invention has an industrial advantage of recycling residual material, such as a waste from the production of optically active amino acids using acylase.

The production method of optically active amino acids of the present invention can be conducted at a reaction temperature of 4 to 60° C., preferably 10 to 40° C.; at pH 3 to 11, preferably pH 6 to 9; at a substrate concentration of 0.01 to 90%, preferably 0.1 to 30%. The reaction often proceeds in a yield of 50 to 100%. The substrate can be added at once at the start of the reaction, but it is preferable to add the substrate successively or discretely to prevent the substrate concentration from getting too high in the reaction solution.

The optically active amino acids generated can be purified by appropriately combining separation of the bacteria or polypeptides by centrifugation or membrane treatment, solvent extraction, crystallization, etc. For example, D-tryptophan can easily be purified by the following procedures. The reaction solution containing microorganism cells is centrifuged to remove the microorganism cells. Subsequently, polypeptides are removed by ultrafiltration, and the filtrate is dehydrated and concentrated to precipitate the amino acid of interest, which is isolated by filtration.

N-acylamino acid racemase that has the advantage in the industrial production has been provided. Utilizing this enzyme, the present invention provides a method for efficiently producing optically active amino acids with high optical purity by the combination use of NAAR and D- or L-aminoacylase.

Optically active amino acids are useful as intermediates for producing pharmaceuticals.

Any patents, patent applications, and publications cited herein are incorporated by reference.

The present invention will be explained in more detail below with reference to examples, but is not to be construed as being limited thereto.

EXAMPLE 1

Cloning of N-acylamino Acid Racemase

An oligonucleotide probe was prepared based on the nucleotide sequence of the N-acylamino acid racemase gene derived from Amycolatopsis sp. TS-1-60. Southern hybridization was performed using the prepared probe for the chromosomal DNA of Sebekia benihana IFO14309 that was partially digested with five restriction enzymes, revealing that the probe was hybridized to a SmaI fragment of about 5 kbp and an SphI fragment of about 4.5 kbp. The SmaI fragment was then recovered and ligated into the SmaI site of plasmid vector pUC18. DH5α strain of E. coli was transformed with the resulting plasmid to prepare a genomic library. The genomic library was screened with the same probe by colony hybridization, and a single colony exhibiting a positive signal was obtained from about 1000 colonies. The plasmid was extracted from this colony, and then digested with restriction enzyme SmaI, thereby verifying the presence of the insert DNA of about 5 kbp. The same probe was used for Southern hybridization, revealing that the insert DNA is capable of hybridizing to the probe.

Subsequently, the N-acylamino acid racemase gene was specified. The entire nucleotide sequence of the about 5-kbp SmaI fragment of the chromosomal DNA was determined by dideoxy-sequencing. The genes of Actinomycetes are characterized by its GC content of about 70%, which is extremely high among all the living organisms, and by its GC content of nearly 100% at the third position of codons. Based on this characteristic, open reading frames (ORFs) could be predicted by searching for a region where GC content is nearly 100% at the third position of the codons. As a result of testing for the GC content, three ORFs, namely ORF1, ORF2, and ORF3, were predicted in the fragment. ORF2 was found to contain a sequence homologous to the oligonucleotide probe, and was also found to exhibit homology to the N-acylamino acid racemase gene derived from Amycolatopsis sp. TS-1-60. ORF2 is 1104 bp in length, encoding 368 amino acids. The initiation codon of this ORF is ATG; and a sequence presumed to be the SD sequence is found upstream of the initiation codon. ORF2 was amplified by PCR using a pair of primers; one has an NdeI site at the position corresponding to the initiation codon and the other has a BglII site at the position corresponding to a portion downstream of the termination codon. The fragment obtained by this PCR amplification was digested with NdeI and BglII, and then ligated into an expression vector, pET-3c, at a position downstream of the T7 promoter; and thus an expression vector, pET-NR, was prepared.

An E. coli strain, BL21(DE3), was transformed with the resulting plasmid pET-NR to express ORF2 in the transformant. To prevent the expressed polypeptide from being insoluble, the transformant was cultured at 28° C., induced with isopropyl β-D-thiogalactopyranoside (IPTG) with final concentration of 0.01 mM. Cultured cells were collected and lysed, and the supernatant obtained was used as a crude enzyme solution for the enzymatic reaction. The enzymatic reaction was performed by reacting the crude enzyme with the substrate, N-acetyl-D-methionine, in the presence of L-aminoacylase for 5 to 60 hours at 30° C. In this reaction system, NAAR activity was estimated by measuring the amount of L-methionine produced. The enzyme activity was defined as 1 U when 1 μmole of L-methionine was produced in a minute. TLC was used only to confirm the production of methionine. The amount of the amino acid produced was determined by TNBS method. Procedures of TNBS method were as follows: 0.5 ml of 100 mM $Na_2B_4O_7$ was mixed with 0.5 ml of a sample containing the amino acid; then 20 μl of 110 mM TNBS (trinitrobenzenesulfonic acid) solution was added and stirred immediately; after 5 minutes, 2 ml of 100 mM $NaHPO_4$ containing 1.5 mM $Na_2SO_3$ was added to the mixture to stop the coloring reaction; and then absorbance was measured at a wavelength of 420 nm.

EXAMPLE 2

Purification of N-acylamino Acid Racemase From a Transformant

Method:

Preparation of Crude Enzyme Solution

The transformant of *E. coli* was cultured for 24 h at 30° C. (IPTG was added at a final concentration of 0.01 mM four hours after the culture was started). Fifty grams of wet bacterial cells harvested from the culture were suspended in 160 ml of 50 mM Tris-HCl (pH 7.5), and disrupted by sonication (with a power of 190 W for 40 min) (200 ml). The cell lysate was centrifuged at 18,000 rpm for 30 min at 4° C., and the resulting supernatant (190 ml) was used as a crude enzyme solution.

First-Round Ammonium Sulfate Fractionation

A 80%-saturated ammonium sulfate solution (in 50 mM Tris-HCl (pH 7.5)) was added to the crude enzyme solution to adjust the final concentration of the ammonium sulfate to 25% saturation (13% W/V), and the mixture was allowed to stand at 4° C. for 16 hours. After 16 hours, the mixture was centrifuged at 8,500 rpm for 30 min at 4° C. to give a supernatant (250 ml).

First-Round Chromatography Using Butyl-Toyopearl 650M

The supernatant (250 ml) obtained by ammonium sulfate fractionation was loaded onto a column of Butyl-Toyopearl 650M (180 ml) pre-equilibrated with a 25% saturated (13% W/V) ammonium sulfate solution (in 50 mM Tris-HCl (pH 7.5)). After the column was washed, the adsorbed proteins were eluted with 5 volumes (900 ml) of 50 mM Tris-HCl (pH 7.5) using an ammonium sulfate concentration gradient (from 25% to 0%). Fractions exhibiting N-acylamino acid racemase activity were collected (280 ml).

Second-Round Ammonium Sulfate Fractionation

The sample obtained by the first-round chromatography with Butyl-Toyopearl 650M was dialyzed, and 385 ml of the sample was recovered. To this 385-ml sample, a 80%-saturated ammonium sulfate solution (in 50 mM Tris-HCl/pH 7.5) was added to adjust the final concentration of the ammonium sulfate to 25% saturation (13% W/V), and the mixture was allowed to stand for 16 hours at 4° C. After 16 hours, the mixture was centrifuged at 8,500 rpm for 30 min at 4° C. to give a supernatant (545 ml).

Second-Round Chromatography Using Butyl-Toyopearl 650M

The supernatant (545 ml) obtained by ammonium sulfate fractionation was loaded onto a column of Butyl-Toyopearl 650M (180 ml) pre-equilibrated with 25% saturated (13% W/V) ammonium sulfate (in 50 mM Tris-HCl (pH 7.5)). After the column was washed, the adsorbed proteins were eluted with 5 volumes (900 ml) of 50 mM Tris-HCl (pH 7.5) using an ammonium sulfate concentration gradient (from 25% to 0%). Fractions exhibiting N-acylamino acid racemase activity were collected (200 ml).

Superose 12HR

The sample obtained by the second-round chromatography with Butyl-Toyopearl 650M was dialyzed, and 280 ml of the resulting sample was recovered. A 200-μl aliquot of the sample was loaded onto a Superose 12HR column pre-equilibrated with 50 mM Tris-HCl (pH 7.5) containing 0.15 M sodium chloride (flow rate: 0.5 min/ml), and 1.9 ml of the resulting sample that exhibited N-acylamino acid racemase activity was obtained. Total activity and total amount of proteins of the sample were calculated assuming the total volume of the sample was 280 ml.

Figure 2:
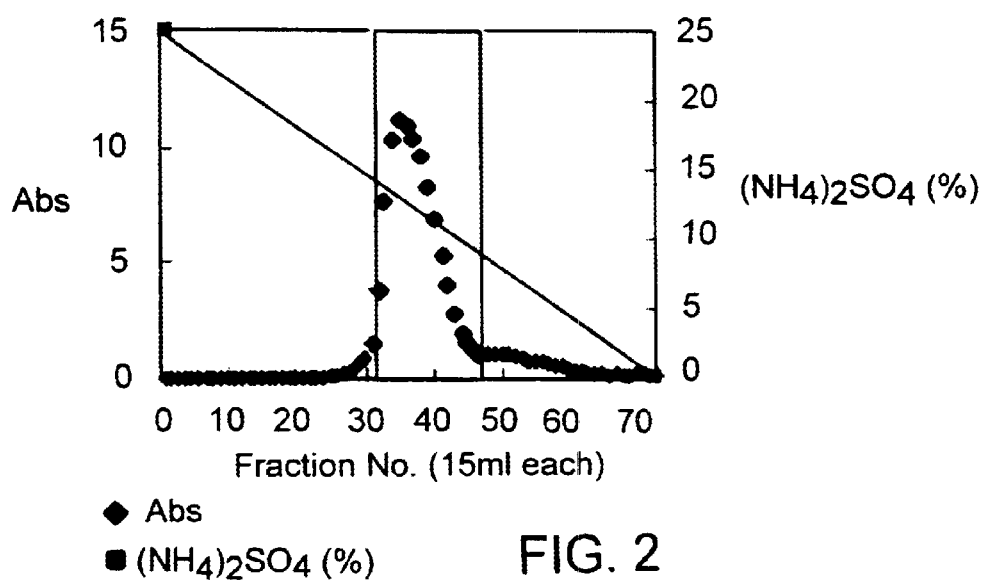
FIG. 2 shows a chromatogram of a second round Butyl-Toyopearl 650M chromatography of the crude enzyme obtained from *E. coli* transformed with an NAAR-expression vector. The left and right handed vertical axes indicate the absorbance at 280 nm and $(NH_4)_2SO_4$ concentration (%), respectively, and the horizontal axis indicates the fraction numbers.
Figure 3:
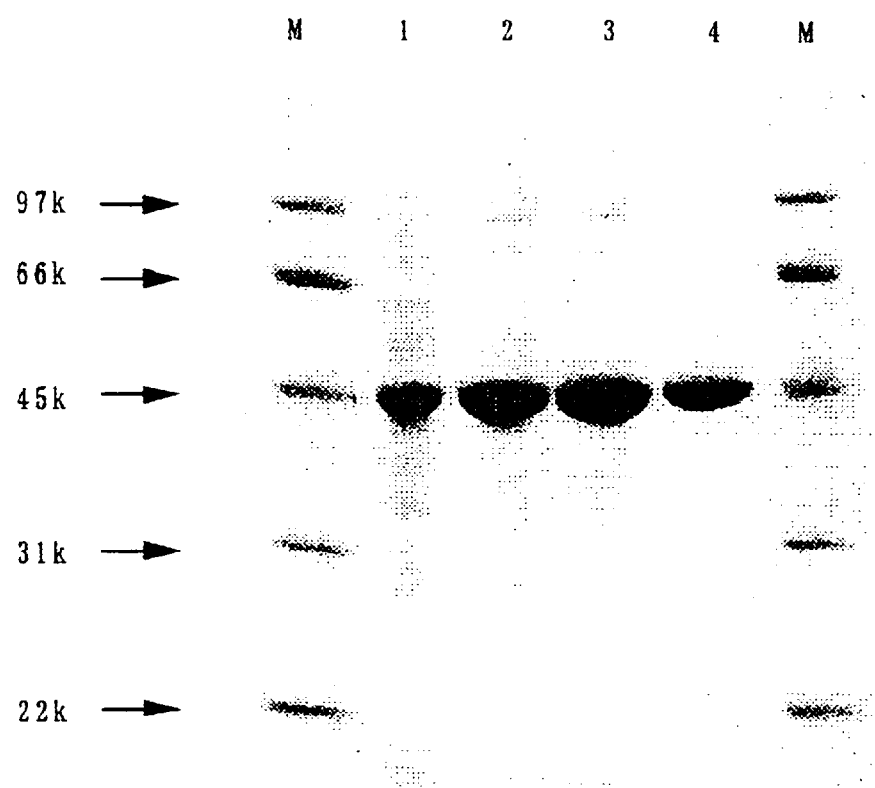
FIG. 3 shows a photograph indicating results of SDS-PAGE for each step of the purification of the crude enzyme obtained from *E. coli* transformed with an NAAR-expression vector. Lane 1, crude enzyme (supernatant of the cell lysate); lane 2, the first round Butyl-Toyopearl 650M chromatography; lane 3, the second round Butyl-Toyopearl 650M chromatography; lane 4, Superose 12HR chromatography; M, molecular weight marker.

The procedure for the purification of NAAR described above are summarized in Table 1, and the results are shown in FIGS. 1 and 2 (chromatograms using Butyl-Toyopearl 650M) and in FIG. 3 (SDS-PAGE before and after the purification). It was confirmed that the NAAR could be purified as a substantially pure protein by two rounds of column chromatography with Butyl-Toyopearl 650M and by chromatography with Superose 12HR.

TABLE 1

| | Total activity (U) | Total protein (mg) | Specific activity (U/mg) | Yield (%) |
|---|---|---|---|---|
| Cell lysate | 4400 | 11760 | 0.37 | 100 |
| Crude enzyme solution (supernatant of cell lysate) | 3876 | 9462 | 0.41 | 88 |
| Butyl-Toyopearl 650M (first-round chromatography) | 3735 | 3080 | 1.21 | 85 |
| Butyl-Toyopearl 650M (second-round chromatography) | 3108 | 2100 | 1.48 | 71 |
| Superose 12HR | 2898 | 1498 | 1.93 | 66 |

EXAMPLE 3

Molecular Weight Determination of N-acylamino Acid Racemase

1. Molecular Weight Determination

Molecular weight of NAAR was determined by (1) gel filtration and (2) SDS-polyacrylamide gel electrophoresis (SDS-PAGE).

(1) Gel Filtration

Figure 4:
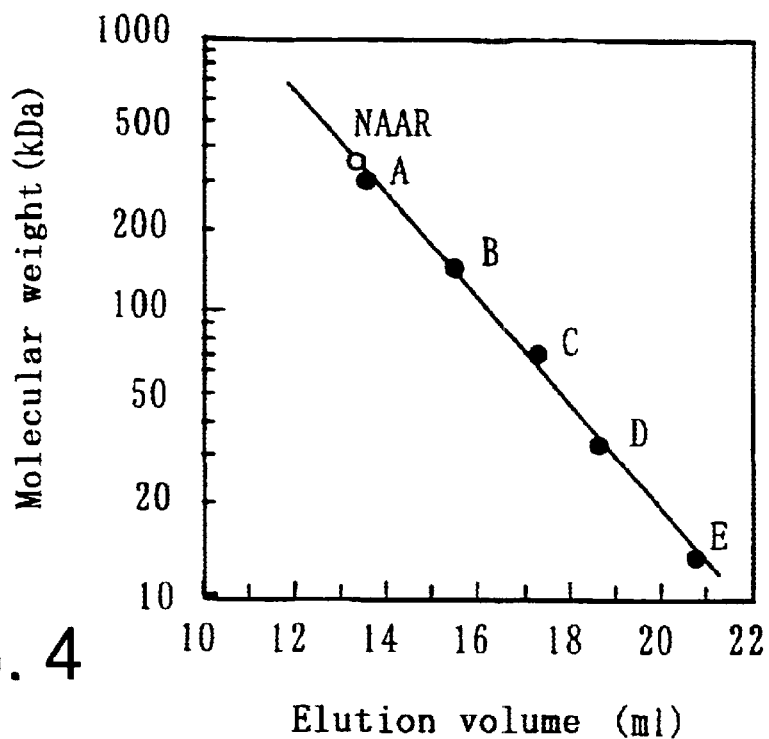
FIG. 4 shows a graph indicating results of molecular weight determination by gel filtration. Molecular weights (kDa) are indicated on the vertical axis, and eluted volume (ml) is indicated on the horizontal axis.

The sample was loaded onto a TSKgel G3000SWXL column (7.8 mm ID×30 cm; TOSOH Co.) pre-equilibrated with phosphate buffer (50 mM, pH 7.0) containing 0.2 M sodium chloride, and the protein was eluted at a flow rate of 0.5 ml/min with 20 ml of the same buffer. Molecular weight markers used were MW-Marker proteins (HPLC) (Oriental Yeast Co.): glutamate dehydrogenase (290,000 daltons), lactate dehydrogenase (142,000 daltons), enolase (67,000 daltons), myokinase (32,000 daltons), and cytochrome C (12,400 daltons). The results suggested that the molecular weight of the enzyme should be about 340,000 daltons (FIG. 4).

(2) SDS-polyacrylamide Gel Electrophoresis

Figure 5:
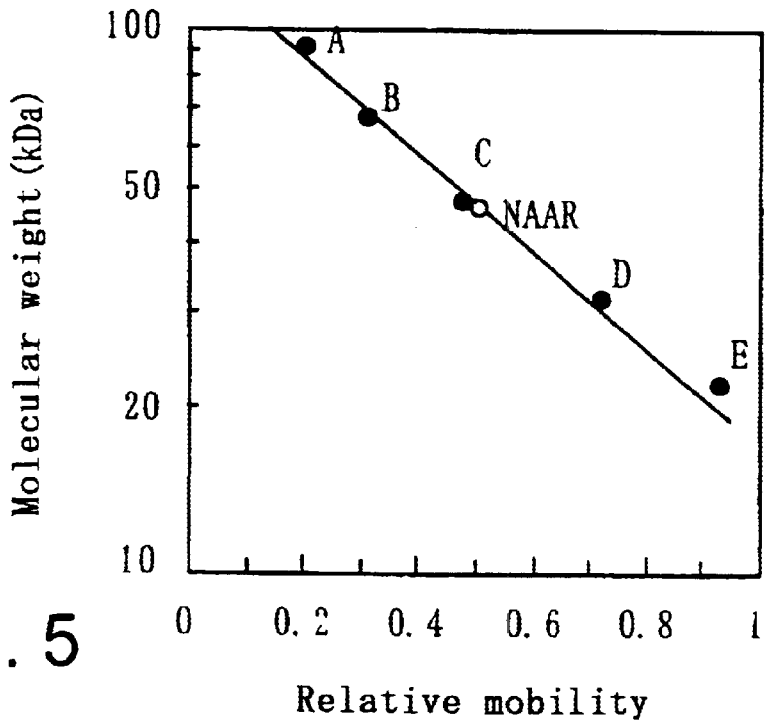
FIG. 5 shows a graph indicating results of molecular weight determination by SDS-PAGE. Molecular weights (kDa) are indicated on the vertical axis, and relative mobility is indicated on the horizontal axis.

SDS-polyacrylamide gel electrophoresis was performed using a apparatus for slab mini-gel electrophoresis (Nippon Eido) according to Laemmli's method (Laemmli, U.K.: Nature, 227, pp.680). Polyacrylamide gel (12%) was used for the gel electrophoresis. To prepare the sample for electrophoresis, the mixture of equal volumes of the enzyme solution and the sample buffer (125 mM Tris-HCl buffer (pH 6.8) containing 4% SDS (sodium dodecyl sulfate), 20% glycerol, 10% 2-ME, and 0.005% Bromophenol Blue (BPB)) was heated at 100° C. for about 5 minutes in a heat block, and then cooled down to room temperature. A 10-μl aliquot of the mixture was subjected to the electrophoresis. Detection of the bands was carried out by Coomassie Brilliant Blue R (CBB-R) staining. Molecular weight markers used were SDS-PAGE Molecular Weight Standards, Low Range (Bio-Rad Co.)); phosphorylase b (97,400 daltons), albumin (66,200 daltons), ovalbumin (45,000 daltons), carbonic anhydrase (31,000 daltons), trypsin inhibitor (21,500 daltons), and lysozyme (14,400 daltons). The results suggested that molecular weight of NAAR is about 44,000 daltons (FIG. 5). NAAR is likely to exist as an octamer because its molecular weight determined by gel filtration is about 340,000 daltons.

EXAMPLE 4

Enzyme Activity Assay for N-acylamino Acid Racemase

The activity of N-acylamino acid racemase was measured by the following method.

First, the following reaction solution was prepared.

| | |
|---|---|
| N-acetyl-D-amino acid (100 mM) | 100 μl (20 mM) |
| cobalt chloride (100 mM) | 5 μl (1 mM) |
| Tris-HCl (0.5 M/pH 7.5) | 50 μl (50 mM) |
| sterile distilled water | 295 μl |
| total | 450 μl |

To this reaction solution, 50 μl of enzyme solution was added, and the 500 μl of the mixture was allowed to react for 5 minutes (or for several ten minutes if the activity was low) at 30° C., followed by heating at 100° C. for 3 minutes to stop the reaction. Subsequently, 3 U of L-amino acylase were added to the mixture, and incubated for 1 hour at 30° C. The mixture was then heated at 100° C. for 3 minutes to stop the reaction.

The amount of L-methionine produced was measured by TNBS method after the reaction was stopped. The enzyme activity was defined as 1 unit (U) when 1 μmole of N-acetyl-L-methionine was produced from N-acetyl-D-methionine in a minute.

EXAMPLE 5

Figure 6:
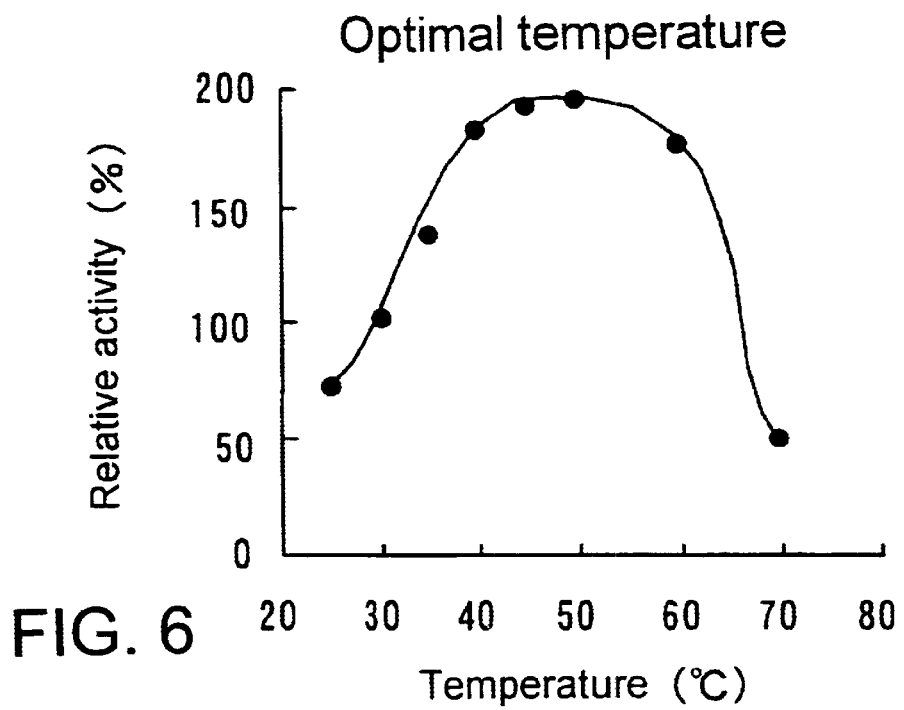
FIG. 6 shows a graph indicating results of analysis of the optimal temperature for NAAR. Relative activity (%) is indicated on the vertical axis, and temperature is indicated on the horizontal axis.
Figure 7:
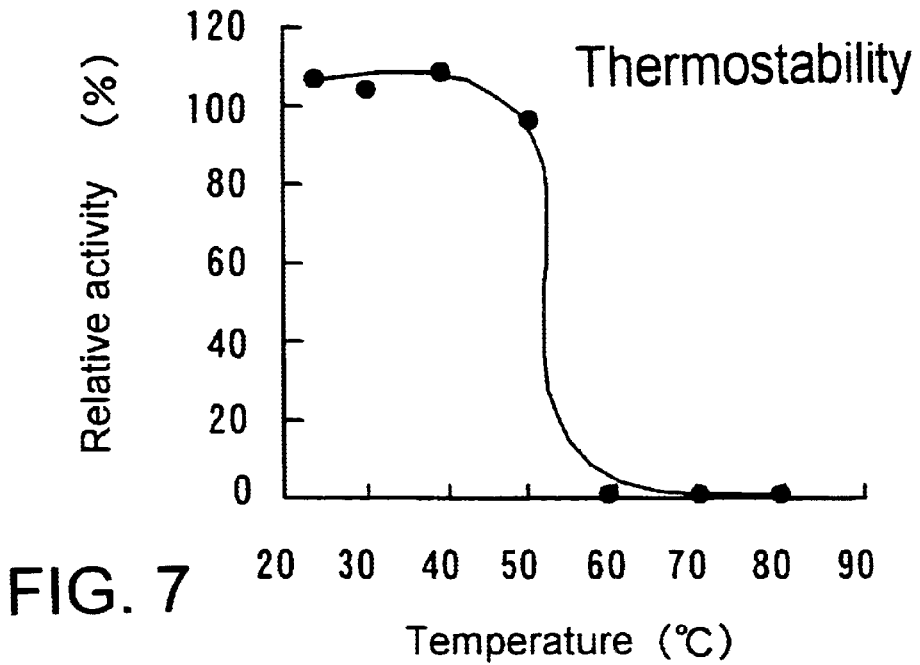
FIG. 7 shows a graph indicating results of analysis of the thermostability of NAAR. Relative activity (%) is indicated on the vertical axis, and temperature is indicated on the horizontal axis.

Optimal Temperature for N-acylamino Acid Racemase and Thermostability of the Enzyme The optimal temperature for the reaction was determined by varying the reaction temperature from 25 to 70° C. and measuring the amount of L-methionine generated during the reaction in the enzyme activity assay. To determine the thermostability of the enzyme, enzyme solution was heated at given temperature for 30 minutes and then immediately cooled on ice to determine the residual activity of the enzyme according to the enzyme activity assay. The enzyme activities in terms of the optimal temperature and thermostability were represented as relative activities (the activity at 30° C. was taken as 100). The results are shown in FIG. 6 (optimal temperature) and FIG. 7 (thermostability). The optimal temperature of NAAR ranged from 40 to 60° C.

EXAMPLE 6

Optimal pH for N-acylamino Acid Racemase and pH Stability of the Enzyme

Figure 8:
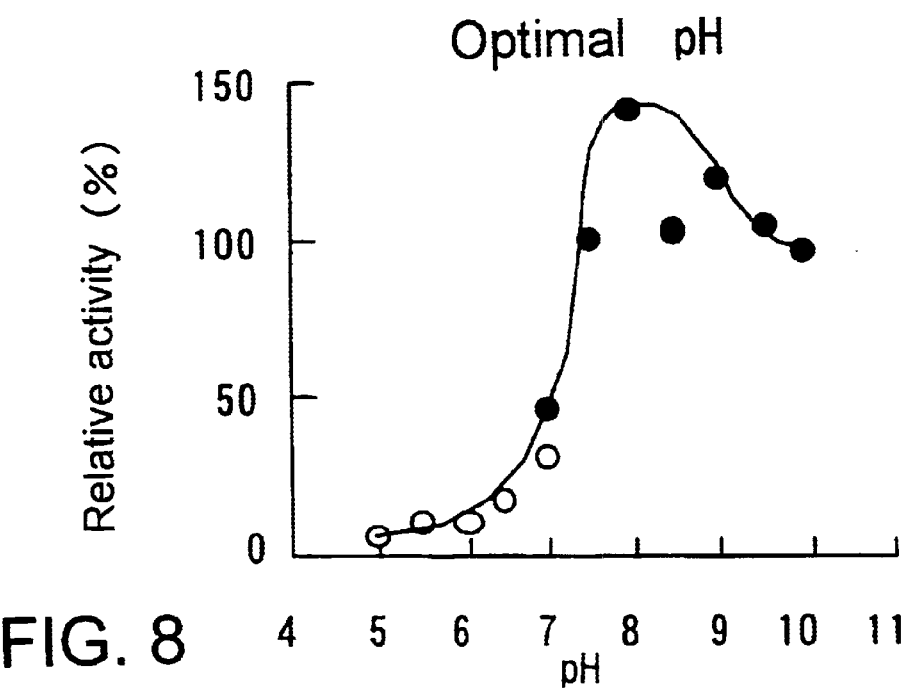
FIG. 8 shows a graph indicating results of analysis of the optimal pH for NAAR. Relative activity (%) is indicated on the vertical axis, and pH is indicated on the horizontal axis.
Figure 9:
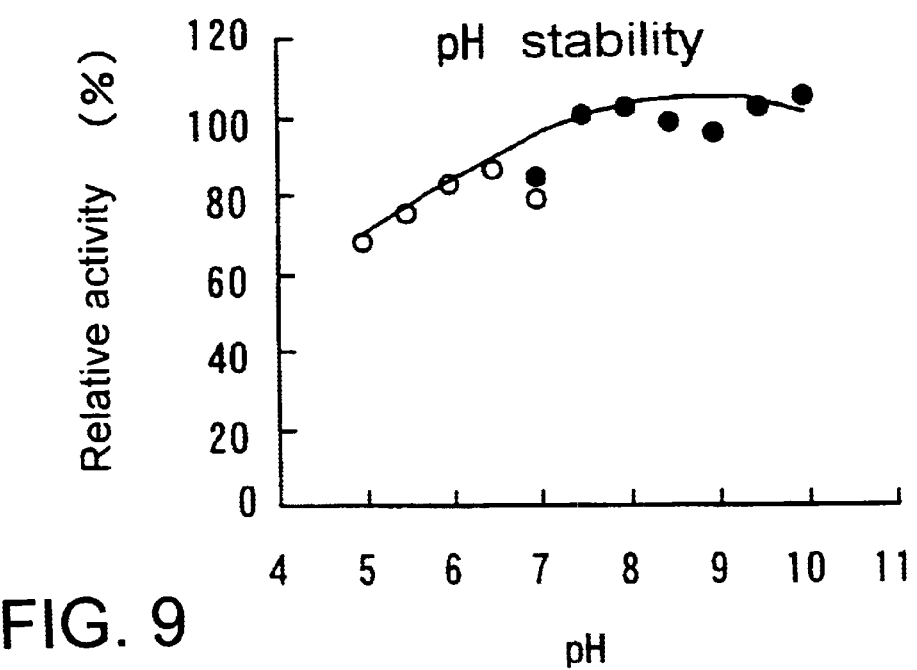
FIG. 9 shows a graph indicating result of analysis of the pH stability of NAAR. Relative activity (%) is indicated on the vertical axis, and pH is indicated on the horizontal axis.

To determine the optimal pH for the reaction, enzyme activities were assayed using bis-Tris-HCl buffer (pH 5.0 to 7.0) and Tris-HCl buffer (pH 7.0 to 10.0) for 30 minutes at 30° C. In the determination of pH stability of the enzyme, the enzyme solution was added (20-fold dilution) to the buffers (the same buffer as used in the determination of optimal pH) with given pH, and, after incubated overnight, the enzyme activities were assayed according to the enzyme activity assay. Enzyme activities were represented as relative activities (the activity at pH 7.5 was taken as 100). The results are shown in FIG. 8 (optimal pH) and FIG. 9 (pH stability). The NAAR was stable within the range of pH 7.5 to 10.

EXAMPLE 7

Substrate Specificity of N-acylamino Acid Racemase

Substrate specificity was determined by measuring enzyme activities according to the above-mentioned enzyme assay, with varying the substrate in the reaction. Enzyme activities were represented as relative activities (the activity on N-acetyl-D-methionine was taken as 100).

| Substrate | Relative activity (%) |
|---|---|
| N-acetylmethionine | 100 |
| N-acetylleucine | 78 |
| N-acetylaspartic acid | 68 |
| N-acctylvaline | 146 |
| N-acetyltryptophan | 69 |
| N-acetylphenylalanine | 74 |
| N-acetylalanine | 86 |

Thus, it was confirmed that the NAAR had the racemizing activity on a wide variety of N-acetyl-amino acids. In particular, it was shown to have relative activity of at least 50 or higher on each of N-acetyl-amino acids: N-acetylalanine, N-acetylaspartic acid, N-acetylleucine, N-acetylvaline, and N-acetyltryptophan when the activity for N-acetylmethionine is taken as 100. An enzymatic reaction system as described below was designed based on this substrate specificity.

EXAMPLE 8

Influence of Metal Ions on N-acylamino Acid Racemase Activity

Influence of various metal ions on N-acylamino acid racemase was examined in the enzymatic activity assay in which cobalt chloride (final concentration 1 mM) to be added was omitted from the reaction solution and instead each ion was added to the reaction at a final concentration of 1 mM. The mixture was incubated for 5 minutes at 30° C., and the amount of L-methionine produced was measured to determine the effect of each metal ion on the N-acylamino acid racemase, using the reaciton solution without any metal ions as a control. The enzyme activities were represented as relative activities, taking the activity in the presence of Co as 100. The results are shown in Table 2. Cobalt ions had effect of activation.

TABLE 2

| Metal ion (1 mM) | Relative activity (%) |
|---|---|
| None | 0 |
| $CoCl_2.6H_2O$ | 100 |
| $ZnCl_2$ | 20 |
| $MnCl_2.4H_2O$ | 60 |
| $FeCl_2.nH_2O$ | 34 |
| $CuCl_2.2H_2O$ | 3 |
| $NiCl_2.6H_2O$ | 37 |
| $CaCl_2.2H_2O$ | 12 |
| $MgCl_2.6H_2O$ | 27 |
| NaCl | 17 |
| $Al_2(SO_4)_3.14\sim18H_2O$ | 3 |
| KCl | 16 |
| $BaCl_2.2H_2O$ | 14 |
| $SnCl_2.2H_2O$ | 9 |
| $FeCl_3.6H_2O$ | 6 |

EXAMPLE 9

Influence of Inhibitors on N-acylamino Acid Racemase Activity

Influence of various enzyme inhibitors on N-acylamino acid racemase was examined in the enzymatic activity assay in which each inhibitor was added to the reaction solution at the final concentration of 1 mM. The mixture was incubated for 10 minutes at 30° C., using the reaction solution without any inhibitors as a control. Excess of L-aminoacylase was added to the reaction solution so that the influence of inhibitors on L-aminoacylase activity was negligible. Enzyme activities were represented as relative activities, taking the activity in the absence of the inhibitors as 100. For EDTA, enzyme activity was measured at a final concentration of 5 mM as well as 1 mM. The results are shown in Table 3. The NAAR activity was inhibited by monoiodoacetic acid, PCMB, and EDTA.

TABLE 3

| Inhibitor | Concentration (mM) | Relative activity (%) |
|---|---|---|
| None | 1 | 100 |
| Hydroxylammonium chloride | 1 | 88 |
| KI | 1 | 97 |
| Monoiodoacetic acid | 1 | 22 |
| p-chloromercuribenzoic acid | 1 | 11 |
| dithiothreitol | 1 | 84 |
| N-ethylmaleimide | 1 | 96 |
| NaF | 1 | 94 |
| 2,2'-Bipyridyl | 1 | 55 |
| Hydrazinium Sulfate | 1 | 69 |
| 1,5-Diphenylcarbonohydrazide | 1 | 68 |
| phenylmethanesulfonyl fluoride | 1 | 84 |
| EDTA | 1 | 10 |
|  | 10 | 0 |

EXAMPLE 10

Racemization of N-acylamino Acid by N-acylamino Acid Racemase

A reaction solution containing 100 mM potassium phosphate buffer (pH 6.5), 1 U of the N-acylamino acid racemase, and 0.5% N-acetyl-L-tryptophan or N-acetyl-D-tryptophan was incubated at 30° C. overnight. Racemization was verified by measuring optical purity of tryptophan in the reaction solution by HPLC. The optical purity of N-acetyltryptophan was determined as follows. N-acetyltryptophan was extracted from the reaction solution with methyl ethyl ketone. After the solvent was removed, the reaction product was resolved by liquid chromatography using an optical resolution column. The measurement was carried out at room temperature, using CHIRALPAK WH (DAICEL CHEMICAL INDUSTRIES, LTD.) as the optical resolution column, and aqueous solution of 0.25 mM cupric sulfate as eluent (flow rate, 1 ml/min; detection wavelength, 254 nm) to determine the quantity and optical purity. As a result, it was shown that N-acetyltryptophan produced from either N-acetyl-L-tryptophan or N-acetyl-D-tryptophan by the method of the present invention was a racemate with optical purity of nearly 0% ee at the end of the reaction.

EXAMPLE 11

Production of D-amino Acid Using N-acylamino Acid Racemase and D-aminoacylase

A reaction solution (100 ml) containing 100 mM potassium phosphate buffer (pH 6.5), 1 U of N-acylamino acid racemase, 1 U of D-aminoacylase, and 15% N-acetyl-DL-tryptophan was incubated at 30° C. overnight. As the reaction progressed, D-tryptophan produced was saturated in the aqueous phase and precipitated upon oversaturation in the aqueous phase, during which process the reaction was continued. The D-tryptophan precipitated in the aqueous phase was separated by filtration, washed with water, and dried (70% recovery). The optical purity of D-tryptophan thus produced was determined as follows. CHIRALPAK WH (DAICEL CHEMICAL INDUSTRIES, LTD.) was used to measure the purity at room temperature using 0.25 mM cupric sulfate as eluent (flow rate, 1 ml/min; detection wavelength, 254 nm). As a result, D-tryptophan with the optical purity of nearly 100% ee was obtained by the method of the present invention.

EXAMPLE 12

Production of L-amino Acid Using N-acylamino Acid Racemase and L-aminoacylase

A reaction solution (100 ml) containing 100 mM potassium phosphate buffer (pH 6.5), 1 U of N-acylamino acid racemase, 1 U of L-aminoacylase (Sigma Co.), and 15% N-acetyl-DL-tryptophan was incubated at 30° C. overnight. As the reaction progressed, L-tryptophan produced was saturated in the aqueous phase and precipitated upon oversaturation in the aqueous phase, during which process the reaction was continued. The L-tryptophan precipitated in the aqueous phase was separated by filtration, washed with water, and dried (70% recovery). The optical purity of L-tryptophan thus produced was determined as follows. CHIRALPAK WH (DAICEL CHEMICAL INDUSTRIES, LTD.) was used to measure the purity at room temperature using 0.25 mM cupric sulfate as eluent (flow rate, 1 ml/min; detection wavelength, 254 nm). As a result, L-tryptophan with the optical purity of nearly 100% ee was obtained by the method of the present invention.

What is claimed is:

1. A method for racemizing an N-acylamino acid, the method comprising contacting an isolated N-acylamino acid racemase with an optically active N-acylamino acid, wherein the racemase comprises a polypeptide selected from the group consisting of:
  (a) a polypeptide comprising the amino acid sequence of SEQ ID NO: 2;
  (b) a polypeptide comprising the amino acid sequence of SEQ ID NO: 2 in which one or more amino acids are substituted, deleted, inserted, and/or added, and having activity of an N-acylamino acid racemase having the enzymatic properties of (1) and (2) below, wherein the number of amino acids that are substituted, deleted, inserted, and/or added, is 30 or less; and
  (c) a polypeptide that has at least 80% sequence identity to SEQ ID NO:2 and has activity of an N-acylamino acid racemase having the enzymatic properties of (1) and (2) below;
    (1) action: the racemase racemizes N-acylamino acids, and
    (2) substrate specificity: the racemase has a relative activity of at least 50 or higher for each of N-acylalanine, N-acylaspartic acid, N-acylleucine, N-acylvaline, and N-acyltryptophan among N-acylamino acids when the activity for N-acylmethionine is taken as 100.

2. A method for racemizing an N-acylamino acid, the method comprising contacting a microorganism producing a racemase, or extract thereof, with an optically active N-acylamino acid, wherein the microorganism is a transformant expressing a polypeptide encoded by a polynucleotide selected from the group consisting of:
  (a) a polynucleotide comprising the coding region of the nucleotide sequence of SEQ ID NO:1;
  (b) a polynucleotide encoding a polypeptide comprising the amino acid sequence of SEQ ID NO:2;
  (c) a polynucleotide that encodes a polypeptide having at least 80% sequence identity to SEQ ID NO:2 and has activity of an N-acylamino acid racemase having the enzymatic properties of (1) and (2) below; and
  (d) a polynucleotide encoding a polypeptide comprising the amino acid sequence of SEQ ID NO:2 in which one or more amino acids are substituted, deleted, inserted, and/or added, and having activity of an N-acylamino acid racemase having the enzymatic properties of (1) and (2) below, wherein the number of amino acids that are substituted, deleted, inserted, and/or added, is 30 or less;
    (1) action: the racemase racemizes N-acylamino acids, and
    (2) substrate specificity: the racemase has relative activity of at least 50 or higher for each of N-acylalanine, N-acylaspartic acid, N-acylleucine, N-acylvaline, and N-acyltryptophan among N-acylamino acids when the activity for N-acylmethionine is taken as 100.

3. A method for producing a D- or L-amino acid, the method comprising racemizing an N-acyl-DL-amino acid by the method according to claim 1 or claim 2 in the presence of a D- or L-aminoacylase.

4. The method of claim 1, wherein the N-acylamino acid racemase is immobilized on a solid surface.

5. The method of claim 1, wherein the polypeptide comprises the amino acid sequence of SEQ ID NO: 2.

6. The method of claim 1, wherein the racemase consists of the polypeptide of (b) and the number of amino acids that are substituted, deleted, inserted, and/or added is 10 or less.

7. The method of claim 1, wherein the racemase consists of the polypeptide of (b) and the number of amino acids that are substituted, deleted, inserted, and/or added is 3 or less.

8. The method of claim 1, wherein the racemase consists of the polypeptide of (b) and comprises the amino acid sequence of SEQ ID NO:2 with conservative amino acid substitutions.

9. The method of claim 1, wherein the racemase comprises the polypeptide of (c) and has at least 90% identity to SEQ ID NO:2.

10. The method of claim 1, wherein the racemase comprises the polypeptide of (c) and has at least 95% identity to SEQ ID NO:2.

11. The method of claim 1, wherein the method is performed at a temperature of about 40° C. to 60° C.

12. The method of claim 1, wherein the method is performed at a pH of about 7.5 to 10.0.

13. The method of claim 2, wherein the polynucleotide is the polynucleotide of (a).

14. The method of claim 2, wherein the polynucleotide is the polynucleotide of (b).

15. The method of claim 2, wherein the polynucleotide is the polynucleotide of (c) and encodes a polypeptide with at least 90% identity to SEQ ID NO:2.

16. The method of claim 2, wherein the polynucleotide is the polynucleotide of (c) and encodes a polypeptide with at least 95% identity to SEQ ID NO:2.

17. The method of claim 2, wherein the polynucleotide is the polynucleotide of (d) and, the number of amino acids that are substituted, deleted, inserted, and/or added, is 10 or less.

18. The method of claim 2, wherein the polynucleotide is the polynucleotide of (d) and, the number of amino acids that are substituted, deleted, inserted, and/or added is 3 or less.

19. The method of claim 2, wherein the polynucleotide is the polynucleotide of (d) and the polypeptide comprises the amino acid sequence of SEQ ID NO:2, with conservative amino acid substitutions.

20. The method of claim 2, wherein the method is performed at a temperature of about 40° C. to 60° C.

21. The method of claim 2, wherein the method is performed at a pH of about 7.5 to 10.0.

22. The method according to claim 1, wherein the N-acylamino acid is at least one N-acylamino acid selected from the group consisting of N-acylalanine, N-acylaspartic acid, N-acylleucine, N-acylvaline, and N-acyltryptophan.

23. The method according to claim 2, wherein the N-acylamino acid is at least one N-acylamino acid selected from the group consisting of N-acylalanine, N-acylaspartic acid, N-acylleucine, N-acylvaline, and N-acyltryptophan.

24. The method of claim 1, wherein the racemase comprises the polypeptide of (c) and is encoded by a polynucleotide that hybridizes under stringent conditions to a DNA consisting of the nucleotide sequence of SEQ ID NO: 1.

25. The method of claim 2, wherein the racemase comprises the polypeptide of (c) and is encoded by a polynucleotide that hybridizes under stringent conditions to a DNA consisting of the nucleotide sequence of SEQ ID NO: 1.

* * * * *

UNITED STATES PATENT AND TRADEMARK OFFICE
CERTIFICATE OF CORRECTION

PATENT NO. : 6,664,083 B2
DATED : December 16, 2003
INVENTOR(S) : Shinji Tokuyama and Akinobu Matsuyama It is certified that error appears in the above-identified patent and that said Letters Patent is hereby corrected as shown below:

<u>Title page,</u>
Item [73], Assignee, please correct from "Daichel Chemical Industries, Ltd" to
-- Daicel Chemical Industries, Ltd. --.

Signed and Sealed this

Fifteenth Day of June, 2004

JON W. DUDAS
*Acting Director of the United States Patent and Trademark Office*